United States Patent [19]

Mandro et al.

[11] Patent Number: 5,533,981
[45] Date of Patent: Jul. 9, 1996

[54] SYRINGE INFUSION PUMP HAVING A SYRINGE PLUNGER SENSOR

[75] Inventors: Marc Mandro, Bow; Jean Bellerose, Manchester, both of N.H.

[73] Assignee: Baxter International Inc., Deerfield, Ill.

[21] Appl. No.: 319,277

[22] Filed: Oct. 6, 1994

[51] Int. Cl.⁶ ................................................. A61M 31/00
[52] U.S. Cl. ............................................................ 604/208
[58] Field of Search ................................... 604/154, 208, 604/30–34, 50–53, 65–67, 118, 207, 151; 128/DIG. 1

[56] References Cited

U.S. PATENT DOCUMENTS

| | | |
|---|---|---|
| 3,858,581 | 1/1975 | Kamen . |
| 3,871,361 | 3/1975 | Kamen . |
| 3,964,139 | 6/1976 | Kleinmann et al. . |
| 4,137,915 | 2/1978 | Kamen . |
| 4,137,916 | 2/1979 | Killman et al. . |
| 4,410,164 | 10/1983 | Kamen . |
| 4,411,649 | 10/1983 | Kamen . |
| 4,424,720 | 1/1984 | Bucchianeri ....................... 128/DIG. 1 |
| 4,544,369 | 10/1985 | Skakoon et al. . |
| 4,600,401 | 7/1986 | Kamen . |
| 4,778,450 | 10/1988 | Kamen . |
| 4,804,368 | 2/1989 | Skakoon et al. . |
| 4,943,279 | 7/1990 | Samiotes et al. . |
| 4,952,205 | 8/1990 | Mauerer et al. .......................... 604/154 |
| 5,236,416 | 8/1993 | McDaniel et al. .................. 128/DIG. 1 |
| 5,254,096 | 10/1993 | Rondelet et al. ......................... 604/152 |
| 5,256,156 | 10/1993 | Kern et al. . |
| 5,256,157 | 10/1993 | Samiotes et al. . |
| 5,295,967 | 3/1994 | Rondelet et al. . |

*Primary Examiner*—Manuel Mendez
*Attorney, Agent, or Firm*—Michael S. Leonard; Francis C. Kowalik; Paul C. Flattery

[57] ABSTRACT

An infusion pump 10 for dispensing fluid from a syringe 22 having a barrel 24 and a plunger 26 slidably inserted into the barrel 24 is disclosed. The infusion pump 10 provides a housing 12 having a bracket 18 which supports the barrel 24. A syringe driver 20 is movably attached to the housing 12 such that the syringe driver 20 abuts the plunger 26 to slide the plunger 26 into the barrel 24. A sensor is provided for sensing both the position of the plunger 26 relative to the barrel 24 and the capture of the plunger 26 in the syringe driver 20. Control circuitry is electrically connected to the sensor for determining the capture and position of the plunger 26.

The sensor comprises a potentiometer 46 attached to the housing 12 and electrically connected to the control circuitry. The sensor further comprises a wiper 44 supported by the syringe driver 20. The wiper 44 operatively contacts the potentiometer 46 such that the control circuitry receives an output signal from the potentiometer to determine the position of the plunger 26 and the capture of the syringe driver 20 in the plunger 26.

17 Claims, 7 Drawing Sheets

SYRINGE INFUSION PUMP HAVING A SYRINGE PLUNGER SENSOR

FIELD OF THE INVENTION

This invention is generally directed to a syringe infusion pump for dispensing fluid medication to a patient. More specifically, this invention is directed to a syringe infusion pump having a sensor to detect the position and capture of a syringe plunger.

BACKGROUND OF THE INVENTION

Syringe infusion pumps are used in the medical field to administer medication to patients. Syringe infusion pumps provide the ability to automatically administer medication over an extended period of time. Thus, patients receive a desired rate of medication administration. Further, medical personnel are free to attend to other duties instead of repeatedly and manually administering medication.

Generally, infusion pumps are fairly well-known in the medical field. Typical syringe infusion pumps utilize a standard syringe pre-filled with a fluid medication. The pre-filled syringe is loaded onto the syringe infusion pump for automatic dispensing of the fluid. Automatic dispensing of the fluid occurs by controlling the insertion of the syringe plunger into the syringe barrel. To control the insertion of the syringe plunger it is desirable to determine the location of the syringe plunger in relation to the syringe barrel. Additionally, it is desirable to detect capture of the syringe plunger in the syringe plunger driving mechanism when the syringe is loaded onto the syringe infusion pump.

Existing infusion pumps have detected the position of the syringe plunger. For example, linear potentiometers, rotary potentiometers, and optical vane techniques have been used in the past. Existing infusion pumps have detected capture of the syringe plunger. However, past devices have provided separate sensing of the plunger position and sensing of the plunger capture. Furthermore, some past devices have utilized an electrical connection to the moving syringe plunger driver. To accomplish an electrical connection to a moving part, those devices have utilized sliding electrical contacts or flying wires, for example. Therefore, a need exists to improve existing infusion pumps by simplifying and combining the functions of sensing syringe plunger position and capture.

The present invention satisfies this need to improve existing infusion pumps. The present invention combines both functions of sensing syringe plunger position and capture. Furthermore, the present invention removes electrical contacts between moving parts of the driving mechanism. Thus, the present invention simplifies infusion pump design, reduces space requirements and potentially reduces manufacturing cost.

Accordingly, one advantage of the present invention is to improve syringe infusion pumps.

Another advantage of the present invention is to sense and determine the position of the syringe plunger.

Another advantage of the present invention is to sense the capture of the syringe plunger.

Another advantage of the present invention is to combine the functions of sensing the position of the syringe plunger and sensing the capture of the plunger.

Another advantage of the present invention is to remove electrical contacts between moving parts of the syringe plunger driving mechanism.

Other advantages and aspects of the present invention will be apparent from reviewing this specification, the drawings, and the claims.

SUMMARY OF THE INVENTION

The present invention provides an infusion pump for dispensing fluid from a syringe having a barrel and a plunger slidably inserted into the barrel. The infusion pump provides a housing having a bracket which supports the barrel. A syringe driver is movably attached to the housing such that the syringe driver abuts the plunger to slide the plunger into the barrel. A sensor is provided for sensing both the position of the plunger relative to the barrel and the capture of the plunger in the syringe driver. Control circuitry is electrically connected to the sensor to determine the capture and position of the plunger. The control circuitry controls the movement of the plunger in the barrel, and thus, controls the dispensing of the fluid from the syringe.

The sensor comprises a potentiometer attached to the housing and electrically connected to the control circuitry. The sensor further comprises a wiper supported by the syringe driver. The wiper operatively contacts the potentiometer such that the control circuitry receives an output signal from the potentiometer to determine the position of the plunger and the capture of the syringe driver in the plunger.

DETAILED DESCRIPTION OF THE INVENTION

Although the present invention can be made in many different forms, the preferred embodiments are described in this disclosure and shown in the attached drawings. This disclosure exemplifies the principles of the present invention and does not limit the broad aspects of the invention only to the illustrated embodiments.

Figure 1:
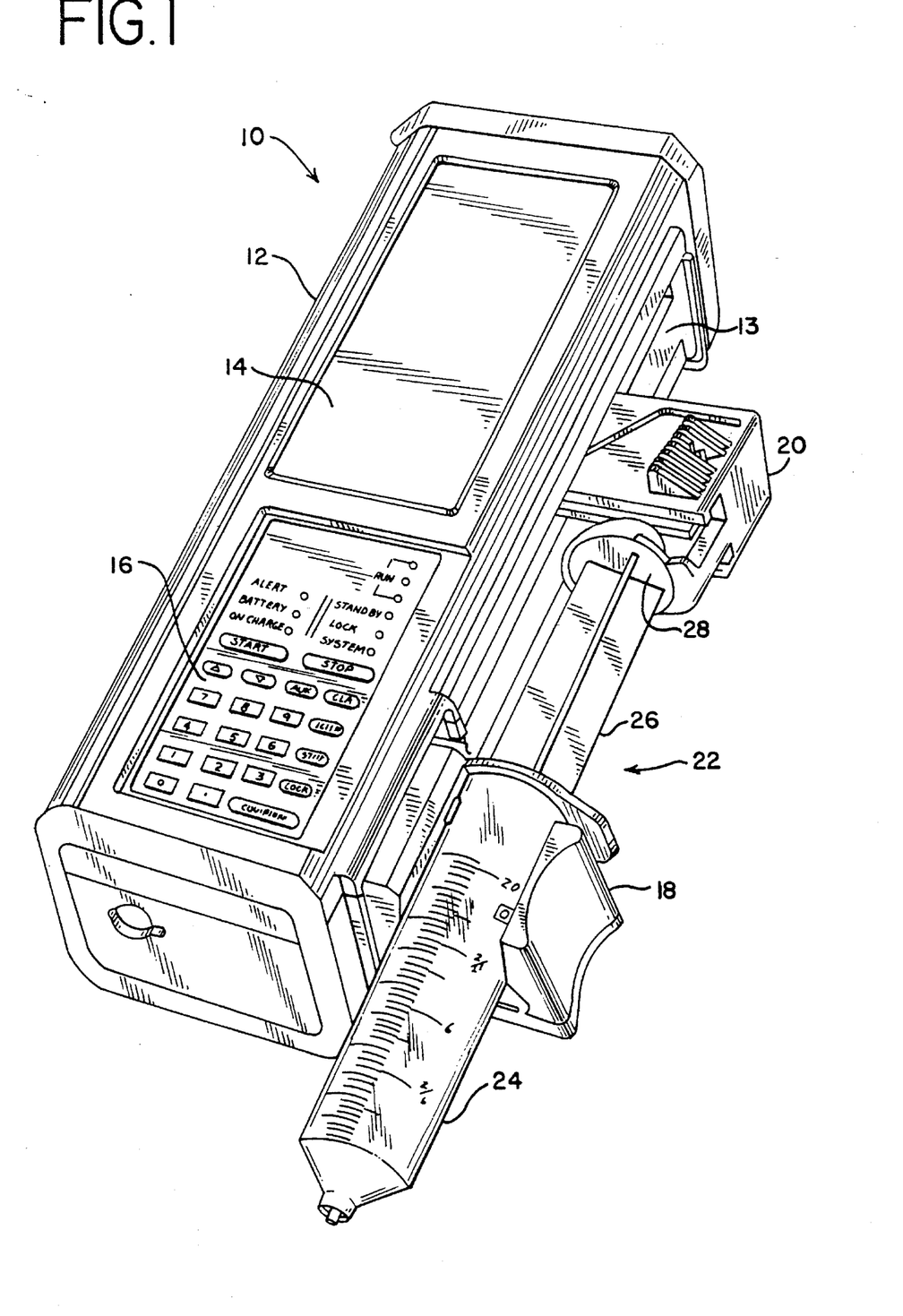
FIG. 1 is a perspective view of a syringe infusion pump made in accordance with the principles of the present invention.

FIG. 1 shows a syringe infusion pump 10 made in accordance with the principles of the present invention. The syringe infusion pump 10 comprises a housing 12, a display screen 14, and a control panel 16. Appropriate control circuitry and a syringe driving mechanism (not shown) are contained within the housing 12. The display screen 14 and the control panel 16 are utilized to set up and operate the infusion pump 10. For reference, in FIG. 1 the syringe infusion pump 10 is shown in a substantially vertical orientation; although, the syringe infusion pump 10 may be positioned in any orientation.

Figure 7:
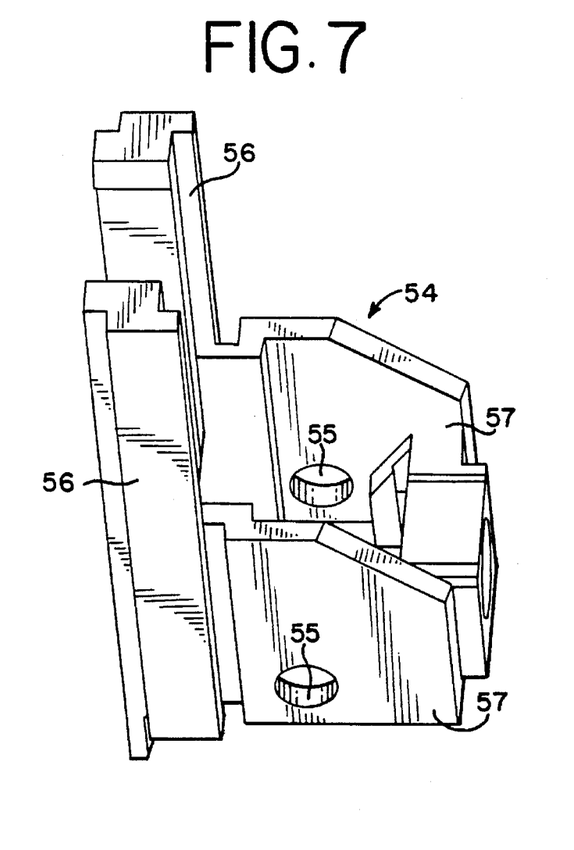
FIG. 7 is a perspective view of a carriage of the syringe driver.

A syringe barrel bracket 18 is attached to a side 13 of the housing 12. A movable syringe driver 20 protrudes from the housing 12 on the same side 13. The syringe driver 20 is slidably engaged with a carriage 54 (the carriage 54 is shown in FIG. 7) of the driving mechanism contained within the housing 12 such that the syringe driver 20 can slide outwardly away from the side 13 and the carriage 54. The carriage 54, as shown in FIG. 7, has a pair of slide rails 56 that slidably engage rail slots 31, shown in FIG. 2, of the syringe driver 20. Referring to FIG. 1, the driving mechanism moves the syringe driver 20 in a linear direction along the side 13 and relative to the bracket 18.

As shown in FIG. 1, a syringe 22 is loaded onto the infusion pump 10. The syringe 22 is a typical syringe having a syringe barrel 24 and a syringe plunger 26. The syringe plunger 26 further comprises an end cap 28 located at the end of the plunger 26 furthest from the barrel 24. The bracket 18 engages the syringe barrel 24 to securely hold the syringe barrel 24 in position. The syringe driver 20 engages the end cap 28 to securely hold the syringe plunger 26 as described below.

Figure 2:
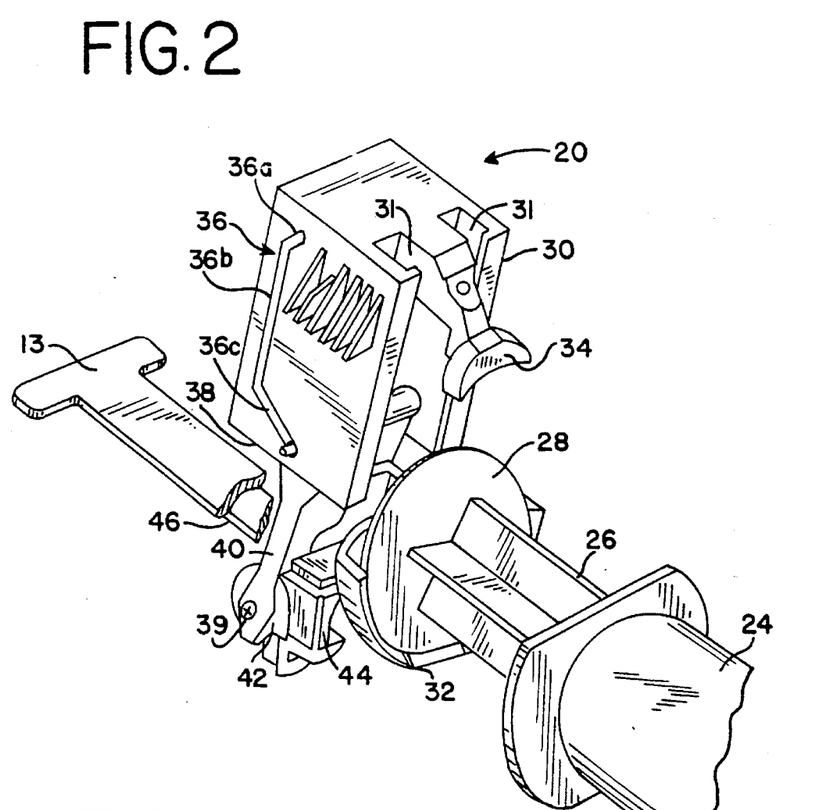
FIG. 2 is a perspective view of a syringe driver of the syringe infusion pump of FIG. 1.
Figure 9:
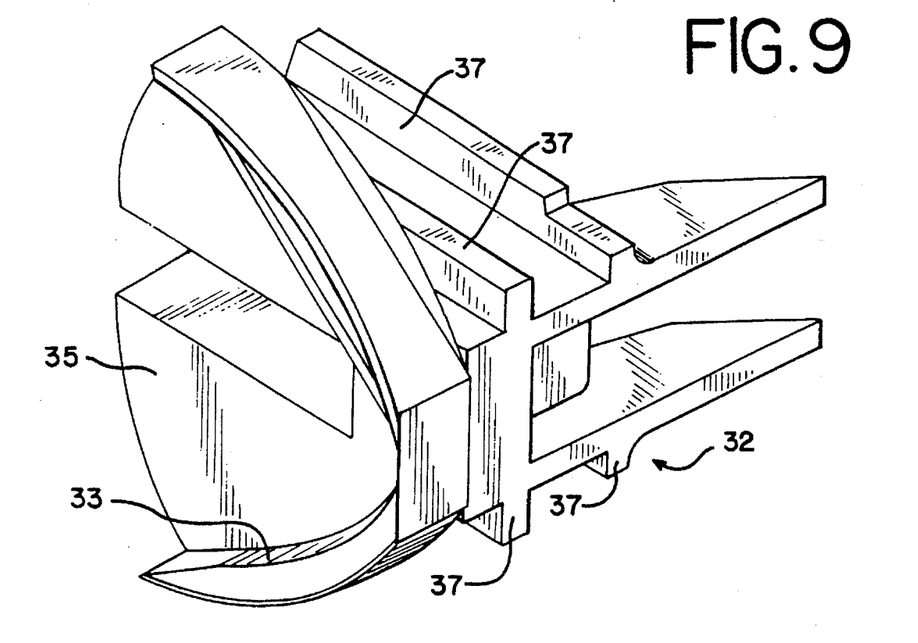
FIG. 9 is a perspective view of a plunger seat of the syringe driver of FIG. 2.

FIG. 2 shows the syringe driver 20 in greater detail. The syringe driver 20 comprises a syringe driver body 30 and a plunger seat 32 slidably engaged with the driver body 30. The driver body 30 has a pair of rail slots 31 for sliding engagement with the carriage 54 and the plunger seat 32. The driver body 30 slides outwardly away from the side 13 and the plunger seat 32; while the plunger seat 32 does not slide away from the carriage 54 or the side 13. Referring to FIGS. 2 and 9, the plunger seat 32 is adapted to support the syringe plunger 26 and more specifically the plunger end cap 28. The plunger seat 32 has a capture wall 33, a pusher wall 35, and slide rails 37. The capture wall 33, along with a plunger clamp 34 on the syringe driver 20 described below, abuts the end cap 28 to securely capture the plunger 26 in the plunger seat 32. The pusher wall 35 abuts the end cap 28 to slide the syringe plunger 26 into the syringe barrel 24. The slide rails 37 slidably engage the rail slots 31 of the driver body 30.

Referring to FIG. 2, a plunger clamp 34 is connected to the driver body 30 and opposes the plunger seat 32. The driver body 30 and the plunger clamp 34 are moved away from the plunger seat 32 to allow the syringe plunger 26 to be positioned in the plunger seat 32. The driver body 30 and, specifically, the plunger clamp 34 are moved into contact with the syringe plunger 26 to securely hold the syringe plunger 26 in the plunger seat 32. Preferably, the plunger clamp 34 is biased toward the plunger seat 32 and against the syringe plunger 26. For example, a spring 58, as symbolically shown in FIG. 10, may bias the plunger clamp 34 toward the plunger seat 32. Preferably, the spring 58 is a constant force spring.

Figure 3:
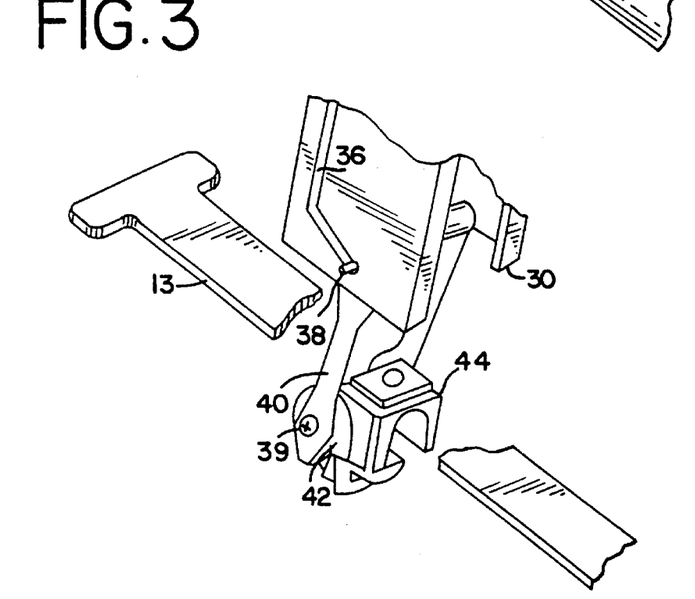
FIG. 3 is a perspective view showing a wiper of FIG. 2 in greater detail.

Referring to FIG. 2, the syringe driver body 30 defines two slots 36 in opposing side walls. Only one slot 36 is shown in FIG. 2. A pin 38 is positioned in the slots 36 and slides along the slots 36 when the driver body 30 is moved away from or back toward the side 13 and the carriage 54. As shown in FIGS. 2 and 3, a lever 40 is connected to the pin 38 within the driver body 30. The lever 40 moves with the pin 38 as the pin 38 slides along the slots 36. The lever 40 rotates around a pin 39 depending on the location of the pin 38 in the slots 36 as described below in regards to FIG. 5. A cam 42 is rotatably connected to the lever 40. A wiper 44 is attached to the cam 42 such that the wiper 44 rotates in conjunction with the cam 42.

Figure 4:
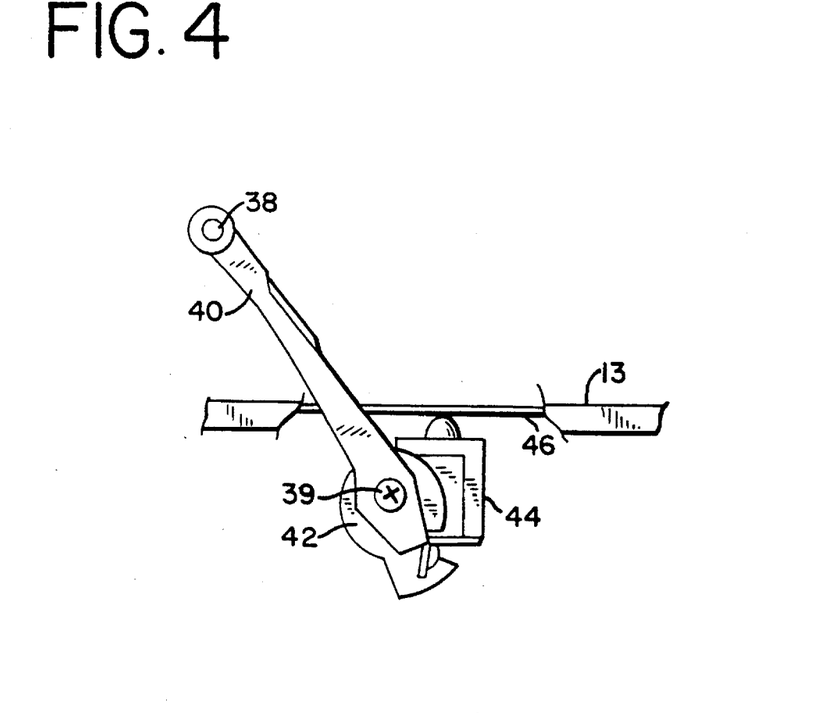
FIG. 4 is a elevational view of the wiper of FIG. 3 showing the wiper in contact with a potentiometer.
Figure 5:
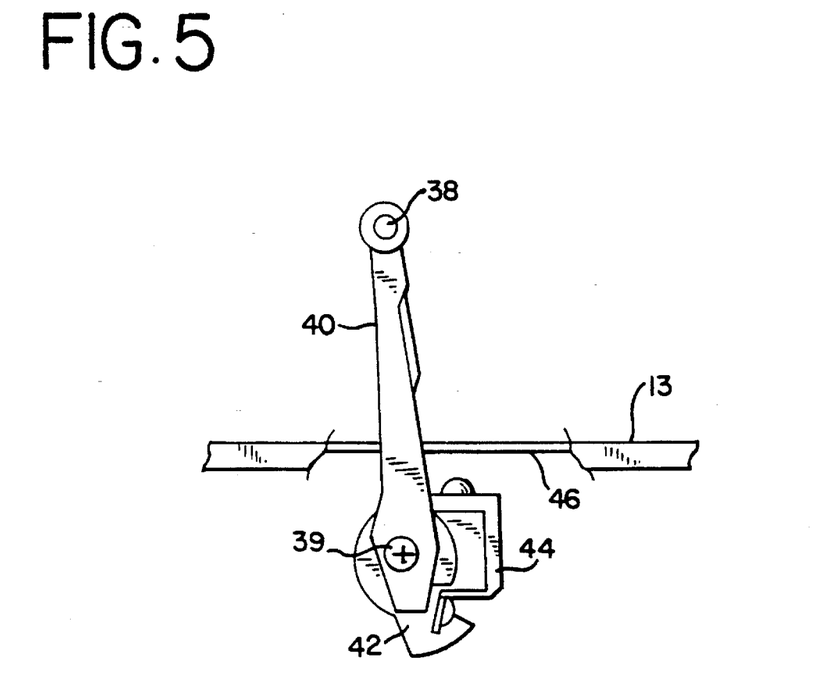
FIG. 5 is an elevational view of the wiper of FIG. 3 showing the wiper not in contact with a potentiometer.
Figure 10:
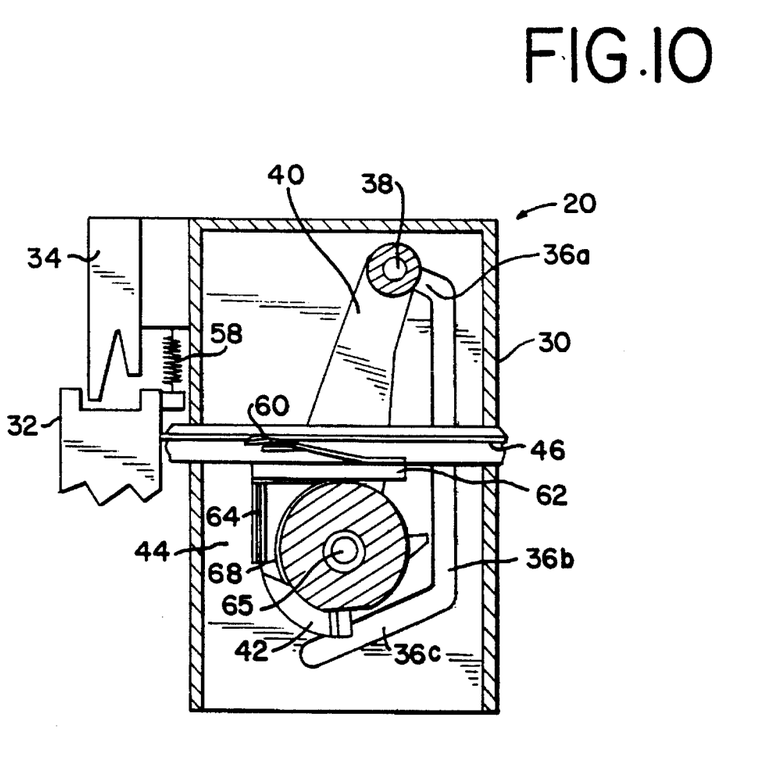
FIG. 10 is a partial cross-sectional view of a syringe driver showing the syringe driver in a syringe unloaded condition.
Figure 11:
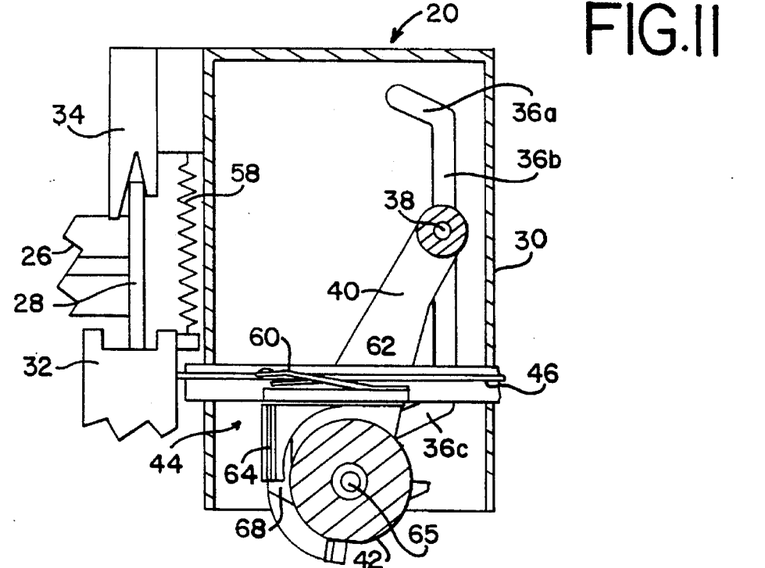
FIG. 11 is a partial cross-sectional view of a syringe driver showing the syringe driver in a syringe loaded condition.
Figure 12:
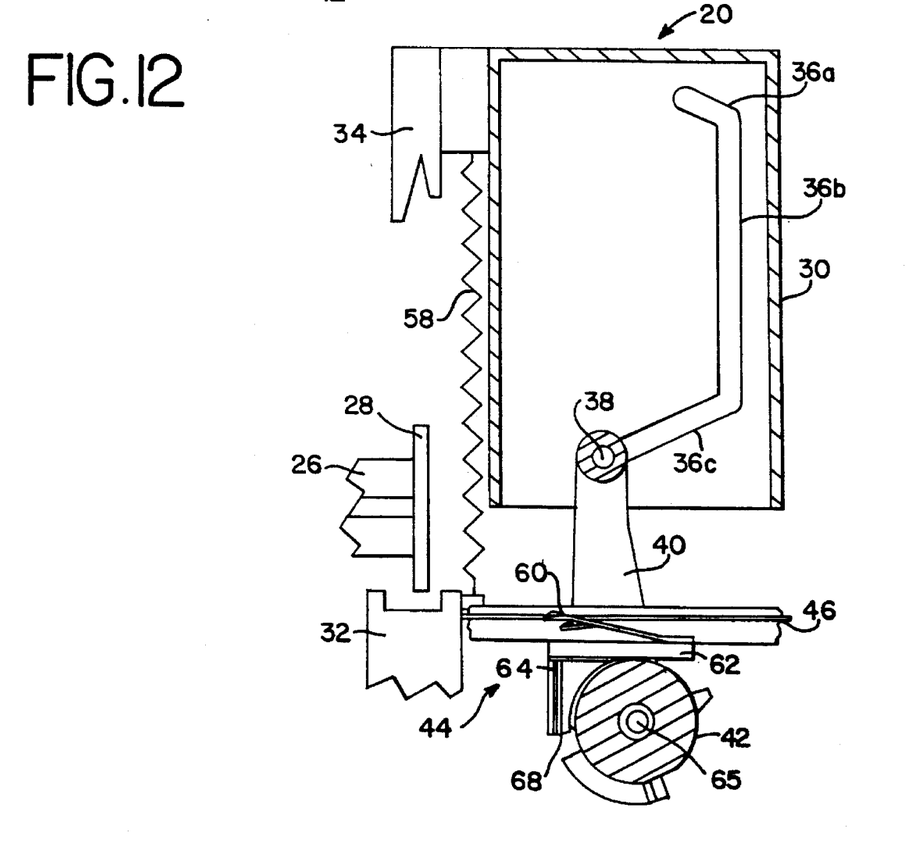
FIG. 12 is a partial cross-sectional view of a syringe driver showing the syringe driver in a syringe loading position.

The slot 36 has a top section 36a, a middle section 36b, and a bottom section 36c. The pin 38 is positioned in the top section 36a when the plunger clamp 34 is biased close to the plunger seat 32, for example, when the syringe plunger 26 is not positioned in the plunger seat 32. In this position the infusion pump 10 is in a syringe unloaded condition as shown in FIGS. 5 and 10. The pin 38 is positioned in the middle section 36b when the plunger clamp 34 is biased against the plunger end cap 28 and the syringe plunger 26 is captured in the plunger seat 32. In this position the infusion pump 10 is in a syringe loaded condition as shown in FIGS. 4 and 11. The pin 38 is positioned in the bottom section 36c when the driver body 30 and the plunger clamp 34 are moved away from the plunger seat 32 to load a syringe 22 onto the infusion pump 10. In this position the infusion pump 10 is in a syringe loading position as shown in FIGS. 5 and 12.

Referring to FIG. 2, a linear potentiometer 46 is attached to the housing 12. The linear potentiometer 46 can be a commercially available potentiometer of the membrane type construction, for example Spectra Symbol, Salt Lake City, Utah provides potentiometers. Preferably, the linear potentiometer 46 is attached to the housing 12 on the inside of the side 13. The linear potentiometer 46 is positioned along the line of travel of the syringe driver 20. When a point force is applied to the linear potentiometer 46, the two membranes of the linear potentiometer 46 touch at that point and complete an electrical connection. The control circuitry of the infusion pump 10 is electrically connected to the linear potentiometer 46. Thus, by using voltage driver techniques, the location of the point force can be determined.

Referring to FIGS. 1 and 2, when the syringe 22 is properly loaded onto the infusion pump 10 the syringe plunger 26 contacts the plunger seat 32. The plunger clamp 34 is biased toward the plunger seat 32 and captures the syringe plunger 26 in the plunger seat 32. When the syringe plunger 26 is properly captured in the plunger seat 32, the pin 38 is positioned in the middle section 36b of the slot 36 such that the wiper 44 operatively contacts the linear potentiometer 46 as shown in FIGS. 4 and 11. As the syringe driver 20 moves along its path of travel, the wiper 44 moves along a corresponding path of travel while contacting the linear potentiometer 46. Thus, the wiper 44 provides the point force applied to the linear potentiometer 46 as discussed above.

FIG. 5 shows the wiper 44 not in contact with the linear potentiometer 46. When the syringe plunger 26 is not positioned on the plunger seat 32 the plunger clamp 34 does not properly capture the syringe plunger 26. Likewise, when the syringe plunger 26 is improperly positioned on the plunger seat 32 the plunger clamp 34 does not properly capture the syringe plunger 26. For example, the plunger clamp 34 may move too close or too far away from the plunger seat 32 depending on the position of the syringe plunger 26. The pin 38 slides to the top section 36a of the slot 36 when the plunger clamp 34 is too close to the plunger seat 32 and the pin 38 slides to the bottom section 36c of the slot 36 when the plunger clamp 34 is too far away from the plunger seat 32. When the pin 38 is positioned in either the top section 36a or the bottom section 36c, the lever 40 rotates about the pin 39 such that the wiper 44 does not contact the linear potentiometer 46.

Figure 8:
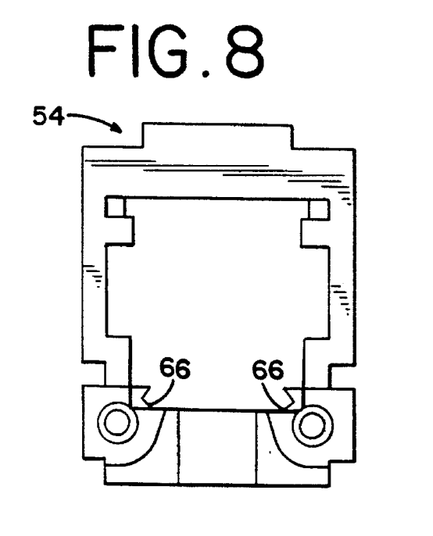
FIG. 8 is a bottom view of the carriage of FIG. 7.

FIG. 10 shows the syringe driver 20 in a syringe unloaded condition. The plunger clamp 34 is positioned close to the plunger seat 32 and the pin 38 is positioned within the top section 36a of the slot 36. Accordingly, the wiper 44 is not in contact with the potentiometer 46. As shown in FIG. 10, the wiper 44 includes a wiper spring 60 and a wiper spring support 62 having slide rails 64. The slide rails 64, orientated as shown in FIG. 10, slide vertically in the rail guides 66 of the carriage 54 shown in FIG. 8. Referring to FIGS. 7 and 10, the lever 40 is rotatably connected to the carriage 54. A hole 65 through the lever 40 is coaxially aligned with the holes 55 in the opposed carriage walls 57. A pair of screws or pins (not shown) are inserted through the holes 55 in the carriage walls 57 and into the hole 65 in the lever 40 such that the lever 40 is positioned between the carriage walls 57. Referring to FIG. 10, as the pin 38 moves into the top section 36a of the slot 36 the lever 40 rotates around the screws in the hole 65, a contact location 68 moves away from the wiper spring support 62, the wiper spring support 62 slides away from the potentiometer 46, and the wiper 44 moves away from the potentiometer 46. The cam 42 described earlier is integral with the lever 40 and thus, does not rotate relative to the lever 40.

Figure 13:
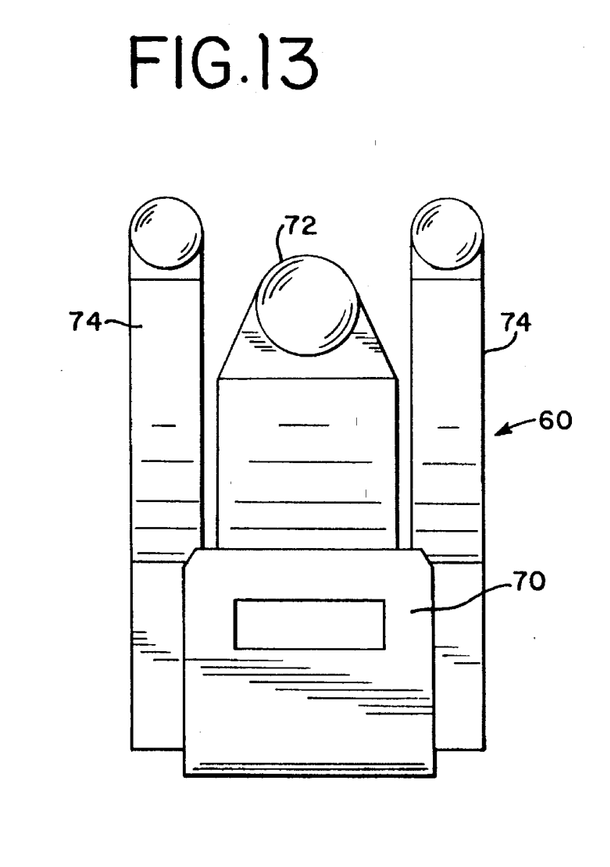
FIG. 13 is a bottom view of a wiper spring of the syringe driver of FIG. 10.
Figure 14:
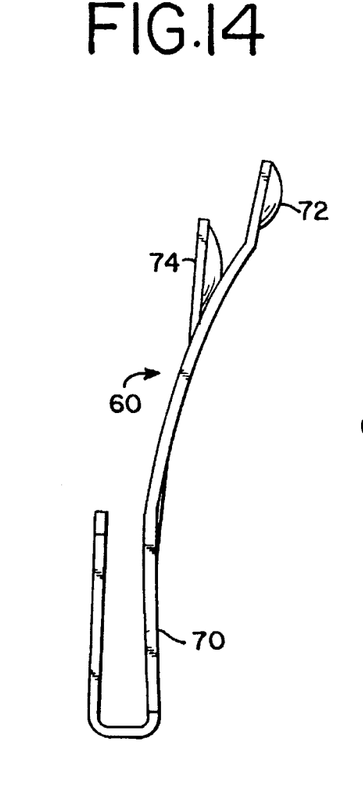
FIG. 14 is a side view of a wiper spring of the syringe driver of FIG. 10.
Figure 15:
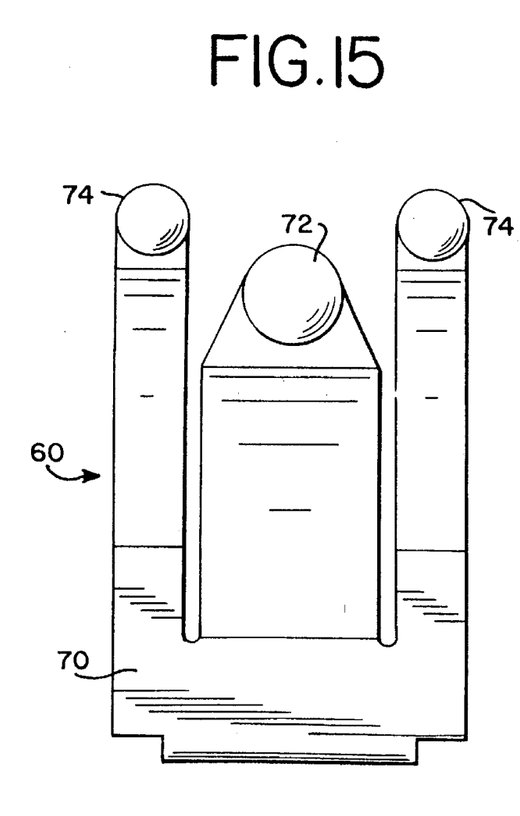
FIG. 15 is a top view of a wiper spring of the syringe driver of FIG. 10.

FIGS. 13, 14, and 15 show a bottom view, a side view, and a top view, respectively, of the wiper spring 60. The wiper spring 60 includes a base 70, potentiometer contact 72, and a pair of arms 74. The base 70 mounts the wiper spring 60 to the wiper spring support 62. The potentiometer contact 72 provides the point force contact on the potentiometer 46. The arms 74 contact the side 13 of the housing 12 to bias the potentiometer contact 72 away from the potentiometer 46. Thus, when the pin 38 is in the middle section 36b of the slot 36 the rotation of the lever 40 imparts a lifting force on the wiper spring support 62 sufficient to overcome the biasing force of the arms 74.

FIG. 11 shows the syringe driver 20 of FIG. 10 in a syringe loaded condition. The syringe plunger 26 is properly captured in the plunger clamp 34 and the plunger seat 32. The pin 38 is positioned within the middle section 36b of the slot 36. Accordingly, the wiper 44 is in contact with the potentiometer 46. As the pin 38 moves into the middle section 36b of the slot 36 the lever 40 rotates around the screws in the hole 65. The lever 40 contacts the wiper spring support 62 at the contact location 68 and slides the wiper spring support 62 toward the potentiometer 46. The wiper spring support 62 moves the wiper spring 60 into contact with the potentiometer 46.

FIG. 12 shows the syringe driver 20 of FIG. 10 in a syringe loading position. The driver body 30 and the plunger clamp 34 have been slid away from the plunger seat 32. Accordingly, the pin 38 is positioned in the bottom section 36c of the slot 36 and the wiper spring 60 moves away from the potentiometer 46 as described in regards to FIG. 10.

In operation of the infusion pump 10, a syringe 22 is properly loaded onto the infusion pump 10 by sliding the driver body 20 and the plunger clamp 34 away from the housing 12 and the plunger seat 32 as shown in FIG. 12. The properly loaded syringe 22 is shown in FIG. 11. As the syringe driver 20 moves along its path of travel, the wiper 44 provides a corresponding point force that moves along the linear potentiometer 46. Through voltage applied to the linear potentiometer 46, the control circuitry determines both that the wiper 44 is contacting the potentiometer 46 and the location of the wiper 44. In this manner, the infusion pump 10 senses the proper capture of the syringe plunger 26 in the plunger seat 32 and determines the position of the syringe plunger 26. The infusion pump 10 uses this information in its operation. For example, this information allows the infusion pump 10 to determine how much fluid is remaining in the syringe 22 and issues any appropriate warning. The infusion pump 10 can also use this information to move the syringe driver 20 at a desired rate. The sensing of the syringe plunger 26 capture and determining of the syringe plunger 26 position is accomplished without an electrical connection to a moving part of the infusion pump 10.

However, if the syringe 22 is not loaded or is improperly loaded onto the infusion pump 10, the wiper 44 does not contact the linear potentiometer 46 as shown in FIG. 10. Through voltage applied to the linear potentiometer 46, the control circuitry determines that the wiper 44 is not contacting the potentiometer 46. In this manner, the infusion pump 10 senses that the syringe plunger 26 is not properly captured in the plunger seat 32. As such, the infusion pump 10 prohibits the syringe driver 20 from moving so that the syringe 22 does not dispense the fluid medication.

Figure 6:
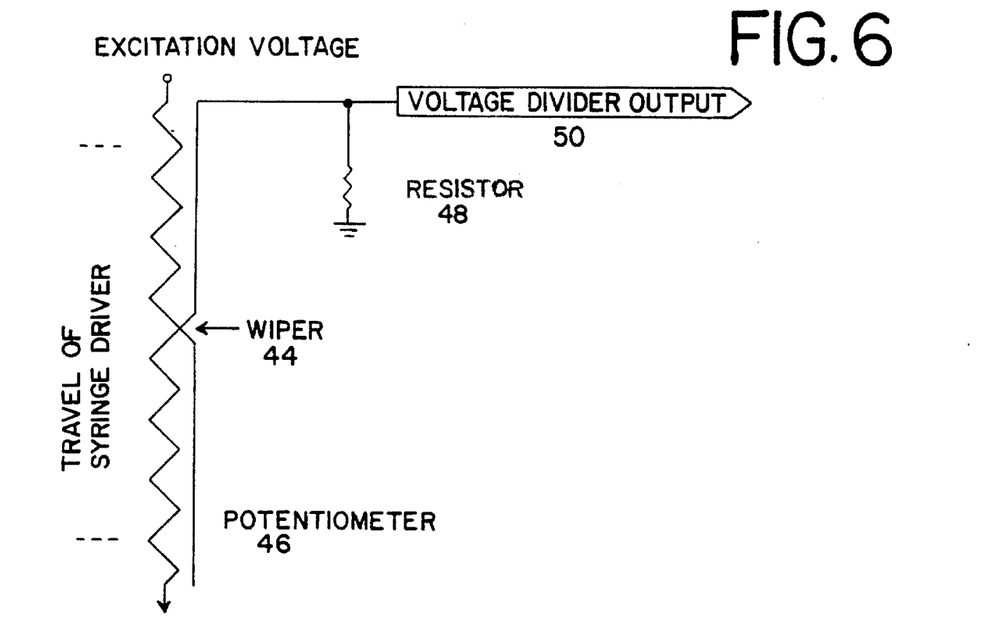
FIG. 6 is a schematic diagram of a portion of the electrical control circuitry for sensing the position and capture of the syringe plunger in the syringe infusion pump of FIG. 1.

FIG. 6 is a schematic diagram of a portion of the electrical control circuitry for sensing the position and the capture of the syringe plunger 26. The control circuit of FIG. 6 is electrically connected to additional control circuitry (not shown) of the infusion pump 10. As discussed above, the wiper 44 contacts the linear potentiometer 46 at a point when the syringe 22 is properly loaded onto the infusion pump 10. The contact point moves along the linear potentiometer 46 as the wiper 44 moves along the line of travel of the syringe driver 20. The linear potentiometer 46 is also electrically connected to a resistor 48. The resistor 48 is electrically connected to a voltage divider 50.

During operation of the infusion pump 10, an excitation voltage is applied to the linear potentiometer 46. When the wiper 44 contacts the linear potentiometer 46 the voltage divider sends an output signal. The output signal is used to determine the capture and the position of the syringe plunger 26. When the wiper 44 moves off of the linear potentiometer 46 the voltage divider 50 output would otherwise be undefined and unpredictable if not for the resistor 48. The resistor 48 forces the output to approximately ø volts when the wiper 44 is moved off of the linear potentiometer 46.

The voltage divider 50 output can range between ø volts and the excitation voltage. By convention, the lower the voltage of the voltage divider 50 output, the closer the syringe driver 20 is to its end of travel. The linear potentiometer 46 is significantly longer than the length of travel of the syringe driver 20 and the wiper 44. This ensures that when the syringe driver 20 reaches its end of travel the voltage divider 50 output is significantly greater than ø volts.

The infusion pump 10 control circuitry is designed to discriminate between the nominal ø volts resulting from a lifted wiper 44 and the intermediate voltages normally seen from the voltage divider 50 when the wiper 44 contacts the linear potentiometer 46. If the voltage divider 50 output is approximately ø volts and the infusion pump 10 attempts to infuse, the infusion pump 10 will stop and an alarm will sound to warn the operator that the syringe plunger 26 is not correctly positioned. If the voltage divider 50 output is an intermediate value, delivery is allowed.

In other embodiments of the infusion pump 10, the membrane linear potentiometer 46 may not be used. For example, an open air potentiometer is attached to the infusion pump 10. The wiper 44 and the open air potentiometer are electrically connected to the control circuitry. When the wiper 44 contacts the open air potentiometer, an electrical connection is completed. When the wiper 44 moves away from the open air potentiometer, the electrical connection is broken.

The infusion pump 10 is adapted to utilize various sizes of syringes 22. The syringe barrel bracket 18, the plunger seat 32, and the plunger clamp 34 are shaped and sized to accommodate various sizes of syringes 22. Typically, the diameter and the length of the syringe barrel 24 determine the size of the syringe 22. Accordingly, the syringe barrel bracket 18, the plunger seat 32, and the plunger clamp 34 are sized to accommodate various diameters and lengths of syringes 22. The capture wall 33 and the pusher wall 35 of the plunger seat 32 are large enough to securely hold various sizes of syringe plunger end caps 28. Likewise, the plunger clamp 34 is also large enough to securely abut various sizes of end caps 28. The middle sections 36b of the slots 36 are long enough to contain the pin 38 when various sizes of the end caps 28 are captured in the plunger seat 32. Further, the control circuitry is capable of controlling the dispensing of medication from the various syringe 22 sizes.

While the preferred embodiments have been illustrated and described, numerous changes and modifications can be made without significantly departing from the spirit and scope of this invention. Therefore, the inventors intend that such changes and modifications be covered by the appended claims.

What is claimed is:

1. An infusion pump for dispensing fluid from a syringe, the syringe having a barrel with a plunger slidably inserted into the barrel, the infusion pump comprising:

a housing which supports the barrel;

a syringe driver in movable contact with the housing, the syringe driver abutting the plunger to slide the plunger into the barrel;

means connected to the housing and the syringe driver for sensing both the position of the plunger relative to the barrel and the abutment of the syringe driver with the plunger, the means comprising a single sensor; and a control circuit electrically connected to the means for sensing to control the movement of the syringe driver.

2. The infusion pump of claim 1 wherein the means for sensing comprises:

a potentiometer attached to the housing and electrically connected to the control circuit; and a wiper supported by the syringe driver, the wiper operatively contacting the potentiometer such that the control circuit receives an output signal from the potentiometer to determine the position of the plunger and the abutment of the syringe driver with the plunger.

3. The infusion pump of claim 2 wherein the syringe driver defines a slot, and the infusion pump further comprises:

a plunger seat slidably engaged with the syringe driver, the plunger seat adapted to support the plunger;

a plunger clamp attached to the syringe driver; the plunger clamp engaging the plunger when the plunger is supported by the plunger seat;

means attached to the syringe driver for biasing the plunger clamp against the plunger; and a pin slidably positioned in the slot, the pin sliding in the slot when the syringe driver slides relative to the plunger seat, the pin linked to the wiper such that the wiper moves into contact or out of contact with the potentiometer in relation to the movement of the plunger clamp.

4. The infusion pump of claim 3 further comprising:

a lever rotatably connected to the pin; and a cam connected to the lever, the cam supporting the wiper.

5. The infusion pump of claim 2 wherein the wiper contacts the potentiometer when the syringe driver properly abuts the plunger and wherein the wiper moves away from contacting the potentiometer when the syringe is not loaded on the infusion pump and wherein the wiper moves away from contacting the potentiometer when the syringe driver improperly abuts the plunger.

6. The infusion pump of claim 2 wherein the wiper contacts the potentiometer when the infusion pump is in a loaded condition and wherein the wiper moves away from contacting the potentiometer when the infusion pump is in a unloaded condition and when the infusion pump is in a loading position.

7. The infusion pump of claim 2 wherein the wiper moves along a length of the potentiometer as the syringe driver moves along the housing.

8. The infusion pump of claim 7 wherein the potentiometer is longer than the length of movement of the wiper.

9. The infusion pump of claim 2 wherein the potentiometer is a membrane type potentiometer.

10. The infusion pump of claim 2 wherein the wiper is electrically connected to the control circuit and the wiper electrically contacts the potentiometer.

11. A sensor for determining the capture of a syringe plunger in a plunger seat and the position of the syringe plunger in a syringe barrel, the sensor comprising:

a linear potentiometer having an excitation voltage applied to the linear potentiometer;

a wiper contacting the linear potentiometer at a contact point when the syringe plunger is captured in the plunger seat, the contact point moving along the linear potentiometer as the syringe plunger slides in the syringe barrel; and an output signal from the linear potentiometer, the output signal indicating the capture of the syringe plunger in the plunger seat and the position of the syringe plunger.

12. The sensor of claim 11 wherein the wiper is spaced away from the linear potentiometer when the plunger is not captured in the plunger seat.

13. The sensor of claim 12 wherein the plunger seat is prevented from sliding when the wiper is spaced away from the linear potentiometer.

14. The sensor of claim 11 further comprising:

a resistor electrically connected to the linear potentiometer; and a voltage divider electrically connected to the resistor, the voltage divider having a divider output signal which ranges from a minimum voltage to the excitation voltage.

15. The sensor of claim 14 wherein the divider output signal is greater than ø volts at the end of the syringe plunger insertion into the syringe barrel.

16. The sensor of claim 14 wherein the divider output signal is approximately ø volts when the wiper is spaced away from the linear potentiometer.

17. A method for controlling the dispensing of medication from a syringe loaded onto a syringe infusion pump comprising the steps of:

providing a plunger seat;

positioning a syringe plunger in the plunger seat;

moving a wiper in contact with a potentiometer when the syringe plunger is properly positioned in the plunger seat;

sending an electrical signal from the potentiometer to a control circuit that indicates both the capture of the syringe plunger in the plunger seat and the position of the syringe plunger in the syringe barrel;

sliding the syringe plunger into a syringe barrel to dispense the medication; and moving the wiper along the potentiometer while the wiper contacts the potentiometer.

* * * * *